United States Patent
Berger et al.

(10) Patent No.: US 7,543,477 B2
(45) Date of Patent: Jun. 9, 2009

(54) SENSOR FOR DETECTING PARTICLES

(75) Inventors: Joachim Berger, Winterbach (DE); Rainer Strohmaier, Stuttgart (DE); Detlef Heimann, Gerlingen (DE); Norbert Breuer, Ditzingen (DE); Ralf Wirth, Leonberg (DE); Karl-Franz Reinhart, Weinsberg (DE); Ralf Schmidt, Gerlingen (DE); Walter Bauer, Eberdingen (DE); Kai-Achim Baldenhofer, Stuttgart (DE); Bernard Kamp, Ludwigsburg (DE); Thomas Grau, Mainhardt (DE)

(73) Assignee: Robert Bosch GmbH, Stuttgart (DE)

( * ) Notice: Subject to any disclaimer, the term of this patent is extended or adjusted under 35 U.S.C. 154(b) by 233 days.

(21) Appl. No.: 10/555,517

(22) PCT Filed: Apr. 1, 2004

(86) PCT No.: PCT/DE2004/000677

§ 371 (c)(1),
(2), (4) Date: Sep. 29, 2006

(87) PCT Pub. No.: WO2004/097392

PCT Pub. Date: Nov. 11, 2004

(65) Prior Publication Data

US 2007/0158191 A1     Jul. 12, 2007

(30) Foreign Application Priority Data

May 2, 2003 (DE) .................. 103 19 664

(51) Int. Cl.
*G01N 7/00* (2006.01)

(52) U.S. Cl. .................... 73/23.33; 73/31.05

(58) Field of Classification Search ............. 73/23.33, 73/31.03, 31.05
See application file for complete search history.

(56) References Cited

U.S. PATENT DOCUMENTS

| 4,478,067 A | * | 10/1984 | Ohta et al. | 73/23.31 |
| 4,567,750 A | * | 2/1986 | Artmann | 73/23.33 |
| 4,595,485 A | * | 6/1986 | Takahashi et al. | 204/406 |
| 4,786,476 A | * | 11/1988 | Munakata et al. | 422/98 |
| 5,215,643 A | * | 6/1993 | Kusanagi et al. | 204/412 |
| 5,310,575 A | * | 5/1994 | Friese et al. | 427/126.3 |
| 5,486,279 A | * | 1/1996 | Friese et al. | 204/429 |
| 5,662,786 A | * | 9/1997 | Friese et al. | 204/429 |
| 5,795,545 A | * | 8/1998 | Koripella et al. | 422/94 |
| 5,824,271 A | | 10/1998 | Frank et al. | |
| 6,101,865 A | * | 8/2000 | Meixner et al. | 73/23.32 |

(Continued)

FOREIGN PATENT DOCUMENTS

DE         3935149 A    *   5/1991

(Continued)

OTHER PUBLICATIONS http://en.wikipedia.org/wiki/Alumina, Nov. 24, 2008, pp. 1-3).

*Primary Examiner*—John Fitzgerald
(74) *Attorney, Agent, or Firm*—Kenyon & Kenyon LLP

(57) ABSTRACT

A sensor for detecting particles in a gas flow, in particular soot particles in an exhaust gas flow, includes at least two measuring electrodes, which are positioned on a substrate made of an insulating material. To protect the measuring electrodes, they are covered by a protective layer.

13 Claims, 2 Drawing Sheets

U.S. PATENT DOCUMENTS

| | | | |
|---|---|---|---|
| 6,174,421 B1 * | 1/2001 | Schumann | 204/424 |
| 6,602,471 B1 * | 8/2003 | Sato et al. | 422/88 |
| 6,634,210 B1 | 10/2003 | Bosch et al. | |
| 7,053,425 B2 * | 5/2006 | Sandvik et al. | 257/253 |
| 2004/0089054 A1 * | 5/2004 | Cramer et al. | 73/19.07 |

FOREIGN PATENT DOCUMENTS

| | | | |
|---|---|---|---|
| WO | WO 9105994 A1 * | 5/1991 |
| WO | WO 03006976 A2 * | 1/2003 |

* cited by examiner

SENSOR FOR DETECTING PARTICLES

FIELD OF THE INVENTION

The present invention is directed to a sensor for detecting particles in a gas flow, in particular soot particles in an exhaust gas flow.

BACKGROUND INFORMATION

A sensor of this type is known from practice and is used, for example, for determining the soot concentration of an exhaust gas of a diesel engine. This sensor forms a resistive particulate sensor in which at least two electrodes are positioned on a substrate which is manufactured from aluminum oxide or yttrium-stabilized zirconium dioxide having an insulation layer, for example. The electrodes may be implemented as interdigital comb electrodes. Soot particles which accumulate in the area between electrodes short-circuit the electrodes, through which a decreasing electrical resistance between the electrodes is measurable as the particle and/or soot concentration on the sensor surface increases.

Since the electrodes are subjected directly to the exhaust gas flow, in this known sensor corrosion of the electrodes and contamination of the sensor surface with materials may disadvantageously occur, which may have an interfering effect on the measurement.

In diesel engines in particular, the exhaust gas released into the environment is to have the lowest possible soot particle concentration. To monitor the operating status of the internal combustion engine, it is expedient for this purpose to position a soot sensor in the exhaust system associated with the internal combustion engine in order to thus monitor the operating status of the internal combustion engine. The soot sensor may be positioned upstream or downstream from a soot filter. If it is positioned downstream from the soot filter, function monitoring of the soot filter may also be performed using the soot sensor.

A soot sensor of the type described above is susceptible to breakdown under the conditions existing in the exhaust system, however.

SUMMARY OF THE INVENTION

The sensor according to the present invention for detecting particles in a gas flow, in particular soot particles in an exhaust gas flow in which sensor the measuring electrodes are covered by a protective layer, has the advantage that the electrodes are protected from corrosion in the event of harsh ambient temperatures in particular.

Furthermore, in the sensor according to the present invention, contamination of the sensitive area now formed by the protective layer by undesired materials may be prevented through a suitable material selection and the cross sensitivity of the sensor may thus be reduced.

The sensor according to the present invention, which represents a resistive sensor for conductive particles, may be designed to be positioned in an exhaust system of a motor vehicle having a diesel engine or also for use in the field of household technology in an oil heating system, for example, it being provided with an appropriately designed support depending on the application.

For use in an exhaust system of a motor vehicle, the sensor is, for example, a soot particulate sensor which is a component of an onboard diagnostics system. The sensor may then also be used for monitoring a diesel particulate filter in the exhaust system.

In an advantageous embodiment, the protective layer of the sensor according to the present invention is manufactured from a material which has a lower conductivity than the particles to be detected. If the resistance measurement is to be performed on the sensor as a purely resistive DC measurement, it is expedient to use a high-resistance base material for the protective layer. Thus, for example, in this case the protective layer may be manufactured from an electrically insulating base material, aluminum oxide $Al_2O_3$ or zirconium dioxide $ZrO_2$, for example, which is doped with a conductive material, such as a metal or graphite. Using the conductive material, the conductivity and/or the electrical resistance of the protective layer may be specifically set and optimized in regard to the particles to be detected. At operating temperatures below approximately 300° C., yttrium-stabilized zirconium dioxide may also be used.

Alternatively, it is also possible to manufacture the protective layer from an ion-conducting material, such as silver iodide AgI. In principle, however, any material which has the properties required in the particular application may be used.

If the sensor is to be operated according to an impedance measuring method and DC signals are therefore to be used for the measuring method used, the protective layer may have an electrical resistance which approaches infinity. This is the case for pure aluminum oxide $Al_2O_3$, for example.

It is advantageous if the material of the insulating protective layer has a high dielectric constant and a low thickness. The high capacitance resulting therefrom allows the measurement of an impedance signal dominated by the particle covering even at low measurement frequencies.

In this way, capacitive interference currents which are caused by the capacitance of the substrate are suppressed. Materials which are used for ceramic capacitors, such as doped $BaTiO_3$, are advantageous here.

Particularly favorable measurement results may be achieved if the electrodes are positioned as interdigital comb electrodes on a surface of the substrate. The protective layer then advantageously covers the entire area of the substrate, its thickness being selected at least in the area of the at least two electrodes in such a way that it is at most one-tenth of the distance between the two measuring electrodes. It is thus ensured during operation of the sensor that the electrical conductivity of the sensor area between the two electrodes is essentially predefined by the amount of particles on the protective layer. The protective layer area between the electrodes and the surface of the protective layer has, because of its low thickness, that the resistance between the interdigitals is high in the absence of soot particles. In addition, however, the resistance between the particle, i.e., soot layer, and the interdigital electrodes is low. A favorable ratio between the base signal, in the absence of particles or soot, and the measured signal, in the presence of particles or soot, is thus obtained.

In order to ensure complete edge covering of the electrodes, a filler layer, whose thickness essentially corresponds to that of the measuring electrodes, may additionally be positioned on the substrate in the gap between the electrodes. The filler layer may be manufactured from the same material as the protective layer, or from a different material which represents an electrical insulator.

Furthermore, the protective layer of the sensor may be implemented both in regard to its composition and also in regard to its surface character in such a way that only special particles, such as soot particles, accumulate, while in contrast undesired particles, such as sulfates or phosphates, are repelled. This may be implemented, for example, in that the protective layer and/or its surface has the most nonpolar character possible.

Through the protective layer on the side of the sensor subjected to the gas flow, the surface character is also made uniform for the accumulation of the particles, in particular soot, which is advantageous in relation to the present conditions where the surface alternates between metal and dielectric material.

Furthermore, it is advantageous in regard to the material selection if the substrate is manufactured from a highly insulating material, for example, from a ceramic such as aluminum oxide.

The sensor according to the present invention may be manufactured, i.e., application of the electrodes, the protective layer, and possibly the filler coating by a screen printing method, which is advantageous for reasons of cost. Furthermore, it is expedient if the protective layer may be manufactured by a cofire process. However, manufacturing the protective layer by a postfire process is also conceivable.

Furthermore, the sensor according to the present invention may be provided with a heating element for cleaning the area exposed to the gas flow.

DETAILED DESCRIPTION

Figure 1:
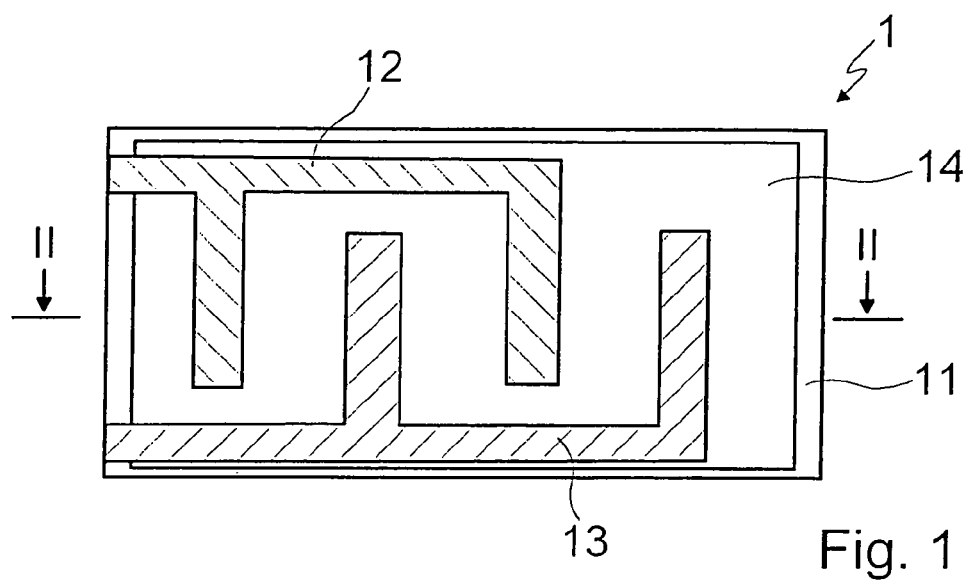
FIG. 1 shows a schematic top view of a soot sensor implemented according to the present invention.
Figure 2:
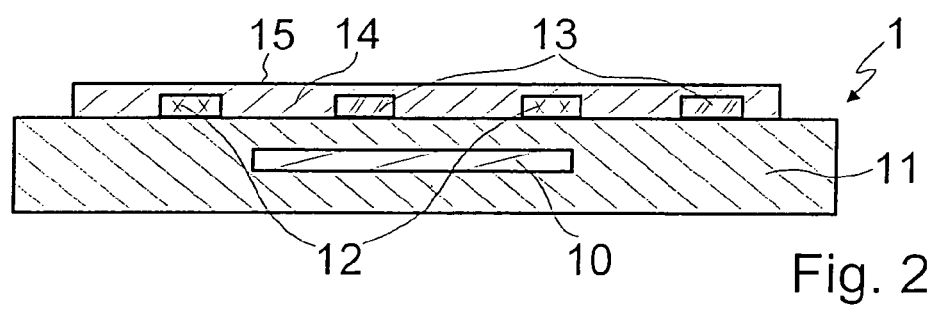
FIG. 2 shows a section through the soot sensor shown in FIG. 1 along line II-II in FIG. 1.

A sensor 1 for detecting particles in a gas flow is illustrated in FIGS. 1 and 2. Sensor 1 is used for installation in an exhaust system of a motor vehicle and is preferably positioned downstream from a soot filter of a motor vehicle having a diesel engine.

Sensor 1 includes a plate-like carrier layer 11, used as the substrate, which is manufactured from a highly insulating material, for example, from a ceramic such as aluminum oxide. It is also conceivable to manufacture carrier layer 11 from an alternative material, such as yttrium-stabilized zirconium dioxide. At high operating temperatures, an additional insulation layer may be necessary for insulation.

A heating element 10, which is only illustrated symbolically here and which is used for burning sensor 1 free of possibly accumulated particles, such as soot particles, is integrated into carrier layer 11.

A structure made of two interdigital comb electrodes 12 and 13, which are manufactured from platinum Pt and are connectable via appropriate contacts to a measuring and control unit, is printed onto carrier layer 11.

Furthermore, sensor 1 has a protective layer 14, which covers measuring electrodes 12 and 13 and carrier layer 11, on the side of comb electrodes 12 and 13, which are used as measuring electrodes.

In the present case, protective layer 14 is made of a high-resistance material, for example, from aluminum oxide $Al_2O_3$, which is admixed with carbon particles and/or flame soot.

The thickness of protective layer 14 is selected in the present case in such a way that in the area of comb electrodes 12 and 13 it is at most one-tenth of the minimum distance between comb electrodes 12 and 13.

Protective layer 14 has an even surface 15, which ensures uniform accumulation of particles over the area of sensor 1.

Figure 3:
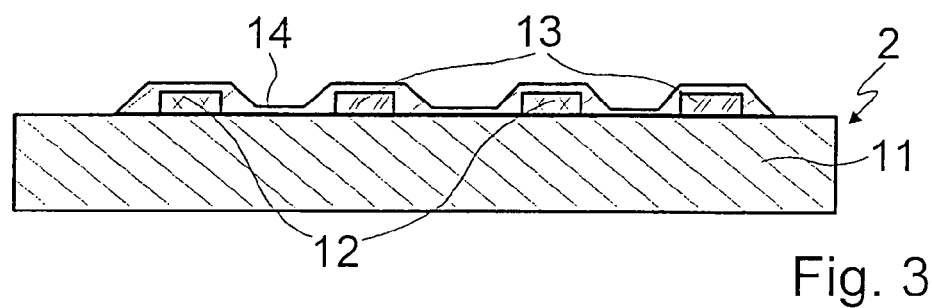
FIG. 3 shows a section through an alternative embodiment of a soot sensor according to the present invention.

An alternative embodiment of a soot sensor 2 is illustrated in FIG. 3, which essentially corresponds to the sensor according to FIGS. 1 and 2, but differs from these in that it has a protective layer 14 which has an essentially constant thickness over its entire area. The measuring area of sensor 11 thus has a profile. Through this measure, an elevation of the electrical resistance of protective layer 14 is achieved in the area between both comb electrodes 12 and 13.

Figure 4:
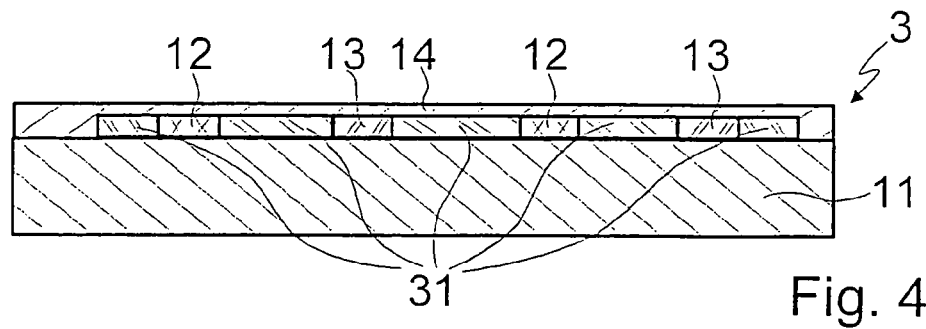
FIG. 4 shows a section through a further embodiment of a soot sensor according to the present invention.

A further embodiment of a soot sensor 3 is illustrated in FIG. 4, which again largely corresponds to the sensor according to FIGS. 1 and 2, but differs from these in that it has a filler layer 31, which is applied to carrier layer 11 in the gaps between comb electrodes 12 and 13 and has the same thickness as comb electrodes 12 and 13. Filler layer 31 is made of a highly insulating material, for example from aluminum oxide. Both filler layer 31 and comb electrodes 12 and 13 are covered by protective layer 14.

Figure 5:
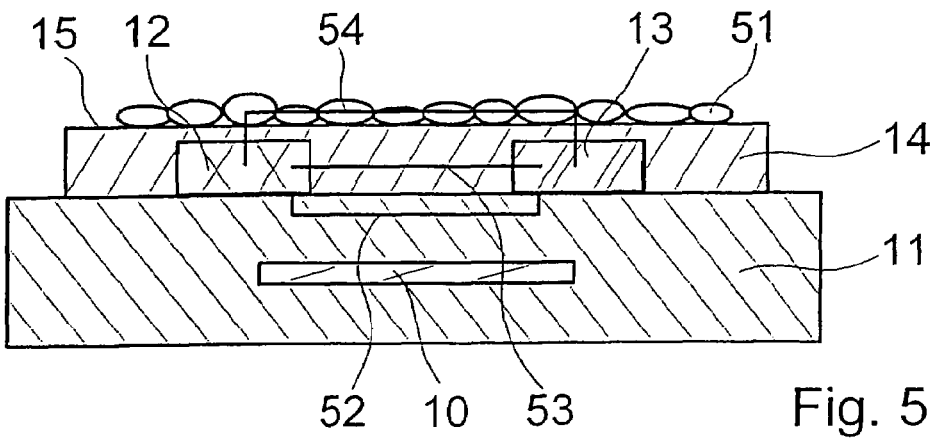
FIG. 5 shows conductor paths in the soot sensor according to FIG. 1.

The sensor shown in FIGS. 1 and 2 is shown in simplified form during operation in FIG. 5, in such a way that soot particles 51 have accumulated on free surface 15 of protective layer 14.

Comb electrodes 12 and 13 are connected to one another via three paths, via a first path 52, which connects them through substrate 11 made of highly insulating material, via a second parallel path 53, which connects comb electrodes 12 and 13 through protective layer 14, and via a third path 54, which connects both comb electrodes 12 and 13 to one another via soot particles 51 accumulated on surface 15 and the particular area of protective layer 14 positioned over comb electrodes 12 and/or 13.

Figure 6:
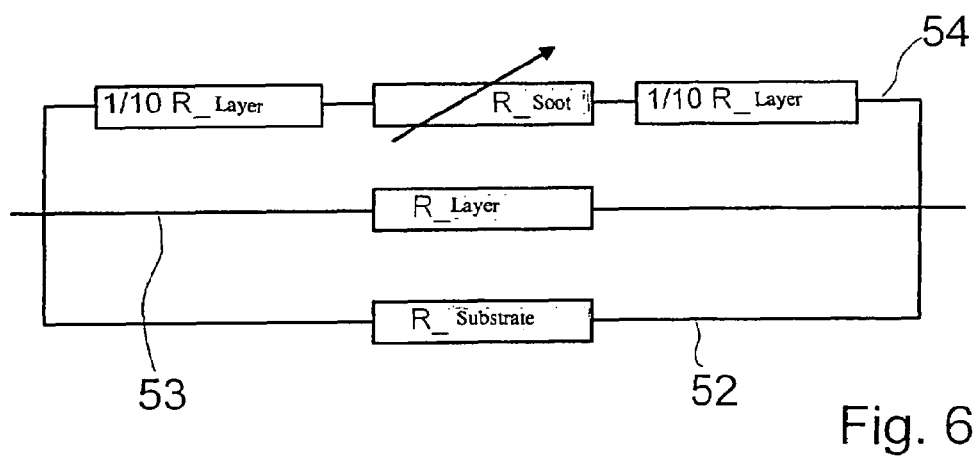
FIG. 6 shows an equivalent circuit diagram for a resistive DC measurement.

The resistance relationships in this sensor are shown on the basis of the greatly simplified equivalent circuit diagram illustrated in FIG. 6. There is a resistance R_substrate in first path 52, which is predefined by the highly insulating material of substrate 11. There is a resistance R_layer in second path 53, which is lower than that of substrate 11, but significantly higher than a resistance predefined by soot particles 51. There is a resistance in third path 54 which results from the resistance of protective layer 14 within the thin area above comb electrodes 13 and 14 and changeable resistance R_soot, which is predefined by the concentration of soot particles 51 on protective layer 14. With growing soot particle concentration on protective layer 14, resistance R_soot is reduced, from which the status of the corresponding exhaust gas may be inferred. Resistances R_substrate and R_layer remain constant.

Figure 7:
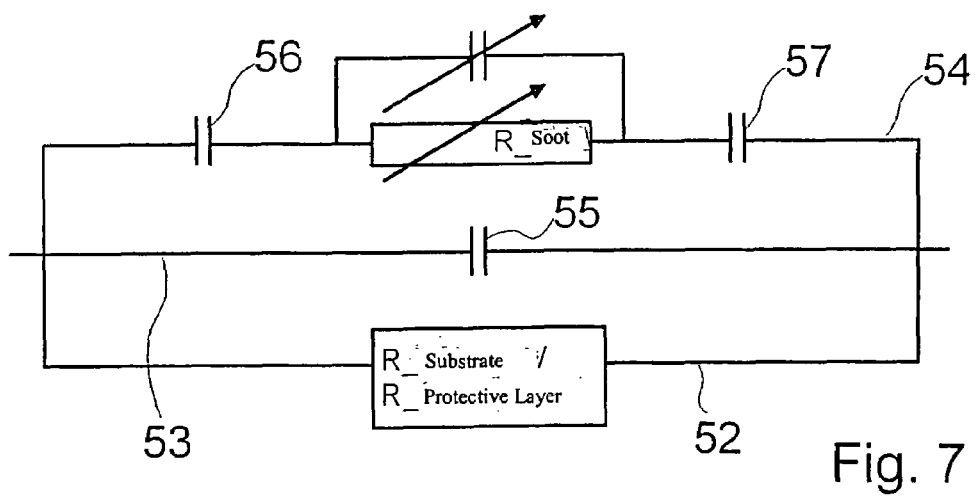
FIG. 7 shows a simplified equivalent circuit diagram for an impedance measuring method.

A greatly simplified equivalent circuit diagram is illustrated in FIG. 7, which indicates the relationships if an impedance measurement is performed using AC signals and a protective layer made of a highly insulating material, such as aluminum oxide $Al_2O_3$, is used. In this case, soot particles 51 form a circuit element having changeable resistance and changeable capacitance, i.e., a circuit element like an RC element. Measuring electrodes 12 and 13 together form a capacitor 55, protective layer 14 and/or substrate 11 acting as a dielectric material. Electrode 12 together with soot particles 51 form a capacitor 56. Electrode 13 together with soot particles 51 form a capacitor 57.

What is claimed is:

1. A sensor for detecting particles in a gas flow, comprising:
   a substrate including an electrically insulating material;
   at least two measuring electrodes positioned on the substrate; and
   a protective layer covering the at least two measuring electrodes; wherein the at least two measuring electrodes are adapted to measure resistance through the protective layer.

2. The sensor as recited in claim 1, wherein the protective layer has an electrical conductivity that is lower than that of the particles to be detected.

3. The sensor as recited in claim 1, wherein the protective layer includes an ion-conducting material.

4. The sensor as recited in claim 1, wherein a thickness of the protective layer at least in an area of the at least two measuring electrodes corresponds to no more than one-tenth of a distance between the at least two measuring electrodes.

5. The sensor as recited in claim 1, further comprising:
   a filler layer positioned between the at least two measuring electrodes and having a thickness corresponding to that of the at least two measuring electrodes.

6. The sensor as recited in claim 1, wherein the at least two measuring electrodes include interdigital comb electrodes.

7. The sensor as recited in claim 1, further comprising:
   a heating element.

8. The sensor as recited in claim 1, wherein:
   the particles include soot particles, and
   the gas flow includes an exhaust gas flow.

9. The sensor as recited in claim 1, wherein the protective layer includes an electrically insulating material that includes one of aluminum oxide ($Al_2O_3$) and zirconium dioxide ($ZrO_2$).

10. The sensor as recited in claim 9, wherein the electrically insulating material is doped with a conductive material including one of a metal and graphite.

11. A sensor for detecting particles in a gas flow, comprising:
    a substrate including an electrically insulating material;
    at least two measuring electrodes positioned on the substrate; and
    a protective layer covering the at least two measuring electrodes; wherein the protective layer includes an electrically insulating material, whereby the electrically insulating material is doped with a conductive material.

12. A sensor as recited in claim 11, wherein the electrically insulating material includes one of aluminum oxide and zirconium dioxide.

13. A sensor as recited in claim 11, wherein the conductive material includes one of metal and graphite.

* * * * *